(12) United States Patent
Rowe

(10) Patent No.: US 9,593,576 B2
(45) Date of Patent: Mar. 14, 2017

(54) METHODS AND SYSTEMS FOR DETERMINING AND USING GAS EXTRACTION CORRECTION COEFFICIENTS AT A WELL SITE

(71) Applicant: Halliburton Energy Services, Inc., Houston, TX (US)

(72) Inventor: Mathew Dennis Rowe, Lafayette, LA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/655,599

(22) PCT Filed: Nov. 25, 2013

(86) PCT No.: PCT/US2013/071668
§ 371 (c)(1),
(2) Date: Jun. 25, 2015

(87) PCT Pub. No.: WO2015/076839
PCT Pub. Date: May 28, 2015

(65) Prior Publication Data
US 2015/0322783 A1    Nov. 12, 2015

(51) Int. Cl.
*E21B 49/08*   (2006.01)
*E21B 21/06*   (2006.01)
(Continued)

(52) U.S. Cl.
CPC .......... *E21B 49/088* (2013.01); *E21B 21/067* (2013.01); *E21B 49/005* (2013.01); *G01N 33/225* (2013.01)

(58) Field of Classification Search
CPC .... E21B 21/067; E21B 49/005; E21B 49/088; G01N 33/225
(Continued)

(56) References Cited

U.S. PATENT DOCUMENTS 4,492,862 A    1/1985  Grynberg et al.
4,887,464 A   12/1989  Tannenbaum et al.
(Continued)

FOREIGN PATENT DOCUMENTS

RU    2459953      8/2012
WO    2010042383 A2   4/2010

OTHER PUBLICATIONS

International Search Report and Written Opinion in related application PCT/US2013/071668, mailed on Aug. 21, 2014. 10 pages.
(Continued)

*Primary Examiner* — John H Le
(74) *Attorney, Agent, or Firm* — John W. Wustenberg; Baker Botts L.L.P.

(57) ABSTRACT

Methods and systems for monitoring, analyzing, and characterizing well bores and reservoir fluids in a subterranean formation are provided. In particular, methods and systems for determining and using correction coefficients for quantitative analysis of gas samples extracted from fluids at a well site based on Fick's laws of diffusion are provided. In one embodiment, the systems include: a gas trap configured to extract one or more gaseous samples from a fluid at a well site; a gas analyzer configured to receive one or more gaseous samples from the gas extraction system and generate data regarding the amount of one or more gas species in the gaseous sample; and an information handling system communicatively coupled to the gas analyzer that is configured to use data received from the gas analyzer to determine an extraction efficiency coefficient for the gas species.

20 Claims, 2 Drawing Sheets

(51) Int. Cl.
*G01N 33/22* (2006.01)
*E21B 49/00* (2006.01)

(58) Field of Classification Search
USPC ... 702/9, 24, 25, 45, 50, 137, 138; 166/370; 175/58
See application file for complete search history.

(56) References Cited

U.S. PATENT DOCUMENTS

| | | |
|---|---|---|
| 5,306,909 A | 4/1994 | Jones et al. |
| 5,648,603 A | 7/1997 | Hanson |
| 5,939,717 A | 8/1999 | Mullins |
| 6,974,705 B1 | 12/2005 | Brumboiu et al. |
| 7,392,138 B2 | 6/2008 | Frechin et al. |
| 8,011,238 B2 | 9/2011 | Hanson |
| 2003/0062472 A1 | 4/2003 | Mullins et al. |
| 2007/0159625 A1 | 7/2007 | DiFoggio |
| 2009/0008560 A1 | 1/2009 | Gunn et al. |
| 2011/0139464 A1 | 6/2011 | Henderson et al. |
| 2013/0036792 A1 | 2/2013 | Tsuduki et al. |
| 2013/0270011 A1 | 10/2013 | Akkurt et al. |
| 2013/0275047 A1 | 10/2013 | Selman et al. |
| 2013/0311096 A1 | 11/2013 | GREER et al. |

OTHER PUBLICATIONS

International Preliminary Report on Patentability issued in related Application No. PCT/US2013/071668, mailed Jun. 9, 2016 (7 pages).

METHODS AND SYSTEMS FOR DETERMINING AND USING GAS EXTRACTION CORRECTION COEFFICIENTS AT A WELL SITE

BACKGROUND

CROSS-REFERENCE TO RELATED APPLICATION

The present application is a U.S. National Stage Application of International Application No. PCT/US2013/071668 filed Nov. 25, 2013, which is incorporated herein by reference in its entirety for all purposes.

The present disclosure relates to subterranean operations and, more particularly, to methods and systems for monitoring, analyzing, and characterizing well bores and reservoir fluids in a subterranean formation.

As oil well drilling becomes increasingly complex, it is desirable to collect and analyze information relating to the formation. One way to collect this information is by analyzing a circulated fluid, such as the drilling fluid. A drilling fluid or "mud" is a specially designed fluid that is circulated in a wellbore or borehole as the wellbore is being drilled in a subterranean formation to facilitate the drilling operation. The various functions of a drilling fluid include removing drill cuttings from the wellbore, cooling and lubricating the drill bit, aiding in support of the drill pipe and drill bit, and providing a hydrostatic head to maintain the integrity of the wellbore walls and prevent well blowouts.

Properties of the drilling fluid are typically monitored during drilling operations. For instance, it is often desirable to accurately measure hydrocarbon gas concentrations of the drilling fluid as it leaves the wellbore. The level of the hydrocarbon gas in the drilling fluid may affect how the well is to be drilled as well as the safety of the drilling rig and personnel involved. Moreover, the concentration of hydrocarbon gases and other components present in the drilling fluid may be indicative of the characteristics of the formation being drilled and the drilling environment. Accordingly, the analysis of drilling fluids and the changes they undergo during drilling operations can be an important factor in optimizing subterranean drilling operations and may be important to the methods of drilling as well as the efficiency of the drilling operations.

One method for collecting and analyzing samples of the drilling fluid involves submerging a rotor within a vessel into the drilling fluid as the drilling fluid exits the wellbore. The drilling fluid is agitated as it enters into and exits out of the vessel and some of the gasses dissolved therein evaporate and escape the confines of the fluid. These extracted gases are then collected and processed by analytical methods to determine the presence and levels of hydrocarbons and other components in the drilling fluid.

However, as a drilling fluid is exposed to a subterranean reservoir containing gases, those gases partition into different fluids present in the wellbore depending on various characteristics of the reservoir. When those fluids are circulated back to the surface, the gas content is often measured by extracting those gases from the fluid. Conventional gas extraction methods generally do not distinguish how the gases (or how much of them) partitioned into different fluids. For example, the existing methods do not measure residual saturation amounts in the aqueous phase, nor do they account for the respective amounts of a component in the oil and aqueous phases.

Indeed, certain conventional techniques of surface well site analysis may result in undesirable phase transitions. Previous endeavors to solve the problem attempted to account for this problem by providing complicated procedures for sampling the fluid in the wellbore itself. However, downhole analysis often requires stopping the circulation in the wellbore, which can lead to several problems. Stopping the circulation can cause economic hardships by delaying production. It can also cause damage as the contents of the wellbore settle.

BRIEF DESCRIPTION OF THE DRAWINGS

These drawings illustrate certain aspects of some of the embodiments of the present disclosure, and should not be used to limit or define the disclosure.

DETAILED DESCRIPTION

Figure 1:
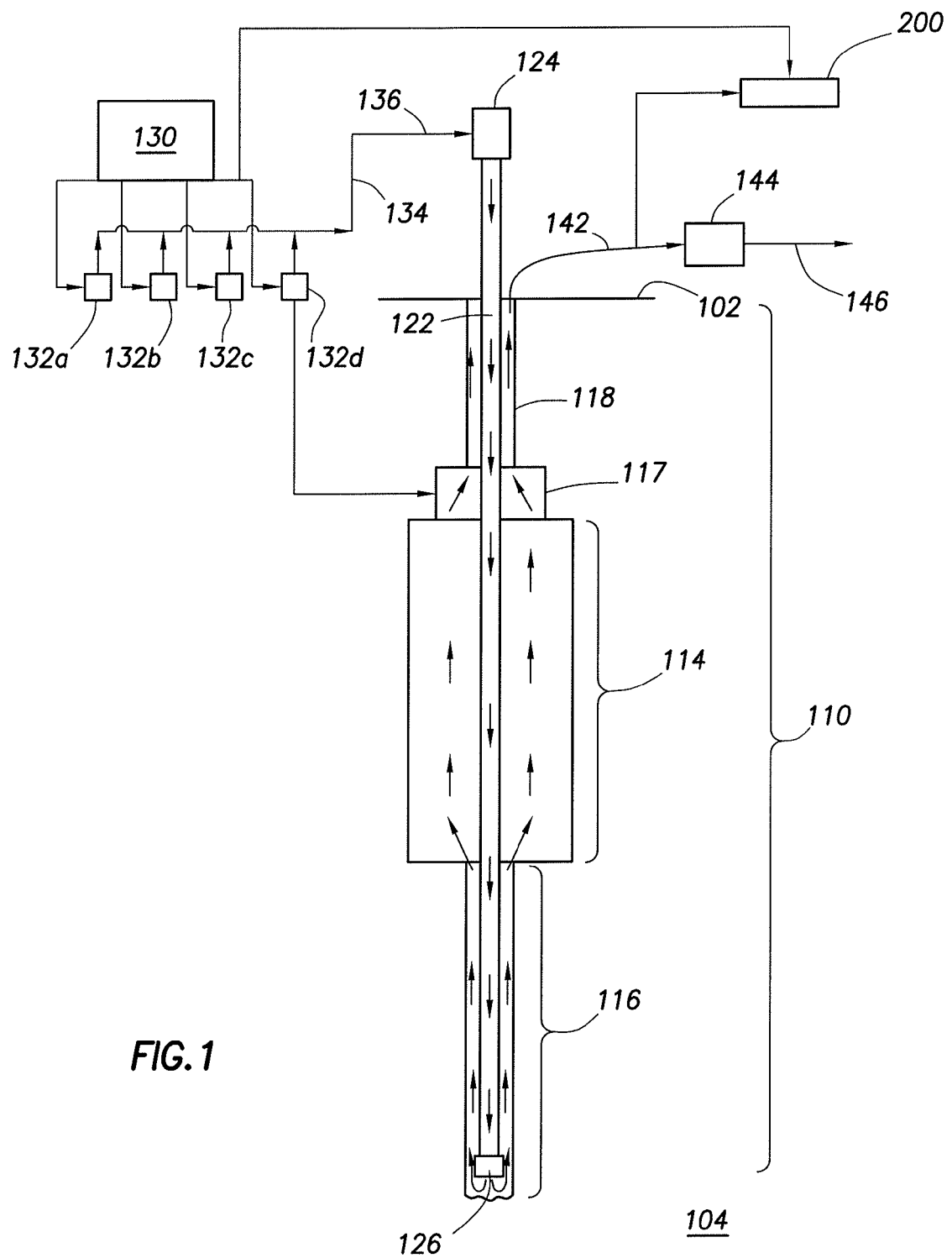
FIG. 1 illustrates an exemplary wellbore and the flow of a circulated fluid within the wellbore.

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer or tablet device, a cellular telephone, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EE- PROM), and/or flash memory; as well as communications media such wires, optical fibers, microwaves, radio waves, and other electromagnetic and/or optical carriers; and/or any combination of the foregoing.

The terms "couple" or "couples," as used herein are intended to mean either an indirect or a direct connection. Thus, if a first device couples to a second device, that connection may be through a direct connection, or through an indirect electrical connection via other devices and connections. The term "communicatively coupled" as used herein is intended to mean coupling of components in a way to permit communication of information therebetween. Two components may be communicatively coupled through a wired or wireless communication network, including but not limited to Ethernet, LAN, fiber optics, radio, microwaves, satellite, and the like. Operation and use of such communication networks is well known to those of ordinary skill in the art and will, therefore, not be discussed in detail herein.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons.

The present disclosure relates to subterranean operations and, more particularly, to methods and systems for monitoring, analyzing, and characterizing well bores and reservoir fluids in a subterranean formation.

The methods and systems of the present disclosure generally involve improved methods of determining and using correction coefficients for quantitative analysis of gas samples extracted from fluids at a well site based on Fick's laws of diffusion. The equation of continuity for gas species α in terms of jα can be expressed according to Equation 1 (general equation) or Equation 2 (Cartesian coordinates) below:

$$\frac{\rho D \omega_\alpha}{Dt} = -(\nabla \cdot j_\alpha) + r_\alpha \qquad (1)$$

$$\rho\left(\frac{\partial \omega_\alpha}{\partial t} + v_x \frac{\partial \omega_\alpha}{\partial x} + v_y \frac{\partial \omega_\alpha}{\partial y} + v_z \frac{\partial \omega_\alpha}{\partial z}\right) = -\left(\frac{\partial j_{\alpha x}}{\partial x} + \frac{\partial j_{\alpha y}}{\partial y} + \frac{\partial j_{\alpha z}}{\partial z}\right) + r_\alpha \qquad (2)$$

where ρ represents fluid density, $\omega_\alpha$ represents mass fraction/concentration of gas species α, $j_\alpha$ represents mass flux of gas species α, and r represents mass rate of production by chemical reaction. Fick's first law relates diffusive flux to concentration under a steady state. Where the primary variable is mass fraction, Fick's first law can be expressed as Equation 3 below:

$$j_i = -\rho D \nabla \omega_\alpha \qquad (3)$$

If Equation 3 is substituted into Equation 2, that may be solved to give Fick's second law, which is expressed as Equation 4 below:

$$\frac{\partial \omega_\alpha}{\partial t} = D \frac{\partial^2 \omega_\alpha}{\partial y^2} \qquad (4)$$

wherein t is time and y is distance. In the methods and systems of the present disclosure, these equations can be used to calculate gas extraction diffusion coefficients at a well site, among other reasons, to provide more accurate quantitative analysis of reservoir fluids.

In one embodiment, a reference sample of a fluid (e.g., a drilling fluid) is circulated in a gas extractor at a well site before it is introduced into a subterranean formation or wellbore. The reference fluid sample is processed in the gas extractor until the maximum amount of gas has been extracted from the sample (i.e., until there is substantially no incremental increase in the amount of gas extracted over time). While the sample is processed, the amount of each gas species α extracted ($\omega_{extracted}$) is measured as a function of time. Applying this measured function to Equation 4 above and integrating that function, the diffusion coefficient D for the sample in the gas extractor can be calculated (y in Equation 4 would correspond to the length of the degassing chamber).

Equation 3 can also be expressed as Equation 3a for each gas species α:

$$j_i = \rho D(\omega_{extracted} - \omega_{original}) \qquad (3a)$$

With the diffusion coefficient D calculated as described above, Equation 3a can be used to calculate the total amount of each gas species α in the reference fluid sample ($\omega_{original}$), with fluid density ρ being measured at the degassing chamber (e.g., using a Coriolis density meter). A correction coefficient $E_\alpha$ reflecting the efficiency of extraction for each gas species α may then be calculated according to Equation 5:

$$E_\alpha = \left(\frac{\omega_{extracted}}{\omega_{original}}\right) \times 100 \qquad (5)$$

Subsequently, when samples of the fluid are analyzed after circulation in a subterranean formation or well bore, the calculated correction coefficient for each gas species $E_\alpha$ may be used, among other purposes, to account for the efficiency of the gas extractor in calculating volumes of each gas species α detected in the circulated samples to account for the extraction efficiency.

Among the many potential benefits of the present disclosure, the methods and systems of the present disclosure may provide greater accuracy in assessing the composition of gases in a fluid sample, and/or the composition of fluids residing in portions of a subterranean formation penetrated by the well bore. The methods and systems of the present disclosure also may reduce or eliminate the need for secondary laboratory analysis to calculate and/or verify correction coefficients. The methods and systems of the present disclosure also may allow for recalculation of diffusion and/or efficiency correction coefficients without additional testing when the chemical and/or physical properties of the drilling fluid and/or extracted gas species vary.

The methods and systems of the present disclosure may be used at a well site where a wellbore is or will be disposed in a subterranean formation. A wellbore may be created so as to extend into a reservoir located in the subterranean formation. In one embodiment, a casing may be disposed within the wellbore and cement may be introduced between the casing and the wellbore walls in order to hold the casing in place and prevent the migration of fluids between the casing and the wellbore walls. A tubing string may be disposed within the casing. In an embodiment, the tubing string may be jointed tubing, coiled tubing, or any other type of tubing suitable for use in a subterranean well environment. Suitable types of tubing and an appropriate choice of tubing diameter and thickness may be known to one skilled in the art, considering factors such as well depth, pressure, temperature, chemical environment, and suitability for its intended use.

The systems and methods of the present disclosure may be used to monitor or characterize fluids and/or subterranean formations in conjunction with any subterranean operation involving the applicable equipment. For example, the systems and methods of the present disclosure may be used in cementing operations, stimulation operations (e.g., fracturing, acidizing, etc.), completion operations, remedial operations, drilling operations, and the like. A person of skill in the art, with the benefit of this disclosure, will recognize how to apply or implement the systems and methods of the present disclosure as disclosed herein in a particular operation.

This analysis described above may be conducted at selected (e.g., predetermined) points in time during an operation, or may be performed continuously throughout one or more wellbore operations. In some embodiments, the analysis described above is performed substantially in or near real-time with one or more wellbore operations. In some embodiments, some or all of the data may be transmitted to an offsite location, for example, where wells at one or more sites may be monitored by the same personnel substantially simultaneously. This may, among other benefits, facilitate more efficient monitoring of wellbore operations because the appropriate personnel may be located offsite. In certain embodiments, data used for and/or generated by the analysis described above may be automatically uploaded into a central database and acquisition system.

FIG. 1 illustrates one example of a typical drilling operation at a rig site in which the present disclosure can be used. In the exemplary drilling operation, a wellbore 110 is drilled from the drill floor 102 to a subterranean formation 104 containing a reservoir. The wellbore may include cased hole 114 and open hole 116. In the cased hole 114, the wellbore 110 is sealed off from the subterranean formation 104 with metal casing, cement, or other means. In the open hole 116, the wellbore 110 is exposed to the subterranean formation 104 and fluids may flow between the wellbore 110 and the subterranean formation 104. A blowout preventer (BOP) stack 117 may be disposed above the cased hole 114. A riser 118 may connect the blowout preventer to the surface. A drill string 122 may be disposed within the wellbore 110. A top drive 124 may rotate the drill string 124 to turn a bit 126 located at the bottom of the drill string 122.

The methods and systems of the present disclosure may be used with any fluid that is circulated in the wellbore 110. During drilling operations, drilling fluid (or "mud") is typically circulated. The drilling fluid or mud may comprise any base fluid, including but not limited to water, oil, synthetic oil and/or synthetic fluid. In certain embodiments, the drilling fluid may further comprise solids suspended in the base fluid. A non-aqueous based mud may contains oil or synthetic fluid as a continuous phase and may also contain water dispersed in the continuous phase by emulsification so that there is no distinct layer of water in the fluid. Such dispersed water in oil is generally referred to as an invert emulsion or water-in-oil emulsion. A number of additives may be included in such drilling fluids and invert emulsions to enhance certain properties of the fluid. Such additives may include, for example, emulsifiers, weighting agents, fluid-loss additives or fluid-loss control agents, viscosifiers or viscosity control agents, and/or alkali.

The density of the drilling mud may be maintained in order to control the hydrostatic pressure that the mud exerts at the bottom of the well. If the mud is too light, formation fluids, which are at higher pressures than the hydrostatic pressure developed by the drilling mud, may enter the wellbore and flow uncontrolled to the surface, possibly causing a blowout. If the mud is too heavy, then the hydrostatic pressure exerted at the bottom of the wellbore may reduce the rate at which the drill bit will drill the hole. Additionally, excessive fluid weights may fracture the formation, which may result in wellbore failures. A person of skill in the art with the benefit of this disclosure will know how to use the appropriate additives to control the weight of the mud.

As shown in FIG. 1, the drilling mud is circulated in the wellbore 110 through the drill string 122. Initially, the drilling mud is pumped to the drill string 122 from an active pit system 130. Several booster pumps 132a-d may be used to help move the drilling mud. The drilling mud may be pumped through a stand pipe 134 and a kelly hose 136 to the top of the drill string 122. The drilling mud is pumped from through the drill string 122 where it exits the drill string 122 through the bit 126 and is circulated in the wellbore 110. As the mud circulates within the wellbore, it interacts with the formation fluids present in the reservoir. The concentration of components of the mud (e.g., hydrocarbons) changes depending on, among other things, the composition of the formation fluid in the reservoir. The drilling mud then flows back up to the surface through the annular space between the drill string 122 and the wellbore 110. When it reaches the surface, the drilling mud flows through a flow out line 142. It passes through a cleaning system 144 before entering a return line 146 that may return the drilling mud to the active pit system 130.

When the mud is returned to the surface, a gas sample is extracted and analyzed in a gas extraction and analysis system 200 as shown in FIG. 1. As shown in FIG. 1, gas extraction system 200 also may be arranged to take, extract, and analyze one or more reference samples from the drilling mud in active pit system 130 before it is circulated in the wellbore. In other embodiments, instead of utilizing gas extraction system 200 to take, extract, and analyze reference samples from active pit system 130, a separate gas extraction apparatus or system (not shown) or separate components thereof may be used to take, extract, and analyze those reference samples. Any suitable gas extractor may be used with the methods and systems of the present disclosure. One example of a suitable gas extractor is described by U.S. Patent Application Publication No. 2011/0219853. Other examples of a suitable gas extractor may include, but are not limited to, the EAGLE™ available from Halliburton Energy Services, Inc. and the Constant Volume Extractor (CVE) gas system available from Halliburton Energy Services, Inc. In certain embodiments, the gas extractor may be designed to operate at constant temperature, pressure, and/or flow. Embodiments that use such a gas extractor can also include the appropriate heaters and flow control valves to ensure that the gas extractor's input stream remains constant. In other embodiments, the gas extractor can use variable flow and variable pressure. Examples of these types of gas extractors may include, but are not limited to, Quantitative Gas Measurement (QGM) systems available from various vendors and suppliers. In these embodiments, it may be desirable to take into consideration the potential change of pressure and flow rate in the analysis.

An exemplary gas extraction and analysis system is system 200, which is illustrated as the block diagram of FIG.

2. In system 200, a delivery pump 204 pumps drilling mud from the mud flow line 202. The delivery pump 204 produces a constant reliable volume of drilling mud from the mud flow line 202 into the system. The delivery pump 204 includes a peristaltic pump. A meter 206 measures the volume of drilling mud that has been extracted from the mud flow line 202 by the delivery pump 204. A heater 208 heats the mud from the meter 206 to a constant mud temperature. The constant mud temperature is selected to liberate hydrocarbon gases, such as alkanes ($C_1$ methane through the hydrocarbon range to $C_{12}$ dodecane), aromatics such as benzene and toluene, and olefins such as ethene (acetylene) and mercaptans. The heater heats the mud to a temperature of approximately (e.g., within 10 percent of) 80 degrees Centigrade.

The mud from the heater 208 is sent to a gas trap 210, which extracts gas from the drilling mud. A sparge gas supply 212 is coupled to the gas trap to introduce an inert gas, such as nitrogen, into the gas trap. The gas trap 210 produces a gas output and a liquid output. The liquid output is sent to a liquid trap 214. A return pump 216 pumps the liquid out of the liquid trap 214 and back into the mud flow line 202. The liquid trap 214 is part of the gas trap 210.

The gas output of the gas trap 210 is sent to a gas analyzer 218, which analyzes the components of the gas output. This gas output is the gas sample. A carrier gas may be added to the gas sample at the point of gas extraction. A carrier gas can be any gas and serves to help pump the gas sample to the gas analyzer. Suitable carrier gases will be known to a person of skill in the art with the benefit of this disclosure and can include atmospheric gas, nitrogen, or helium. The gas analyzer may account for the presence of the carrier gas. Gas analyzer 218 may include any equipment known in the art that is capable of analyzing a gas phase sample. For example, in some embodiments, gas analyzer 218 uses gas spectroscopy. In other embodiments, gas analyzer 218 may include a hydrocarbon analyzer. Other analyzers may include mass spectrometers, laser spectrometers, and infrared spectrometers. In other embodiments, the gas analyzer may include solid state chemical detectors. The gas analyzer 218 reports its results to a controller 220, which also receives data (not shown) from the meter 206.

In certain embodiments, an information handling system may be used to collect, process and display data from a gas analyzer (e.g., gas analyzer 218 in FIG. 2) or data regarding other activities at the well site (either automatically via sensors at the well site or manually entered into the system), perform calculations using that data, as described above, and/or execute instructions to perform various functions at a well site. The information handling system may include any device capable of performing one or more of these functions, such as a programmable logic controller or PLC, a suitably programmed computer, etc. Any suitable processing application software package may be used by the control system to process the data. In one embodiment, the software produces data that may be presented to the operation personnel in a variety of visual display presentations such as a display. In certain example system, the measured value set of parameters, the expected value set of parameters, or both may be displayed to the operator using the display. For example, the measured-value set of parameters may be juxtaposed to the expected-value set of parameters using the display, allowing the user to manually identify, characterize, or locate a downhole condition. The sets may be presented to the user in a graphical format (e.g., a chart) or in a textual format (e.g., a table of values). In another example system, the display may show warnings or other information to the operator when the central monitoring system detects a downhole condition. Suitable information handling systems and interfaces for use in the methods and systems of the present disclosure may include SENTRY™ and INSITE™ provided by Halliburton Energy Services, Inc. Any information handling system or interface may be used in keeping with the principles of this disclosure. In certain embodiments, the different information handling systems may be communicatively coupled through a wired or wireless system to facilitate data transmission between the different subsystems. Moreover, each information handling system may include a computer readable media to store data generated by the subsystem as well as preset job performance requirements and standards.

Figure 2:
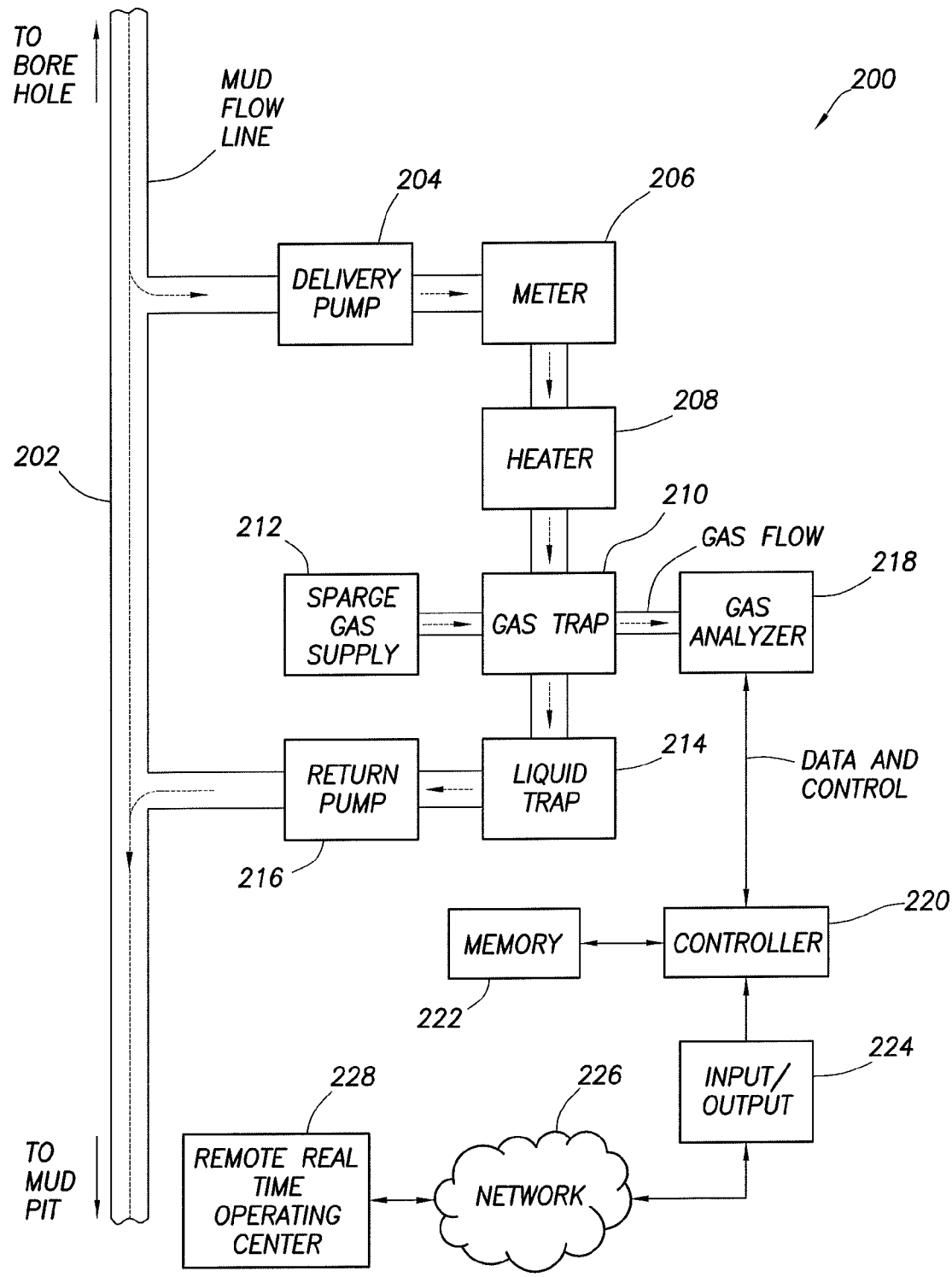
FIG. 2 illustrates one example of a well site gas extraction and analysis system that may be used in certain embodiments of the present disclosure.

For example, referring now to FIG. 2, controller 220 is a special purpose computer programmed to perform the functions described herein. The controller 220 is coupled to a memory 222. The memory 222 contains the programs to be executed as the controller 220 performs its functions as well as constants and variables used to perform those functions. These programs may comprise, among other things, instructions to perform one or more of the calculations used to calculate the correction coefficient $E_\alpha$ reflecting the efficiency of extraction for each gas species $\alpha$, as discussed above. The controller 220 may be coupled to one or more input/output devices 224, such as a keyboard, a mouse, a monitor or display, a speaker, a microphone, or a network interface. The controller 220 also may be communicatively coupled to a network 226, such as a local area network or the Internet, either directly or through one or more of the input/output devices 224, for example, via a satellite, a modem, a router, wired connections, and/or wireless connections. Other information handling systems (e.g., information handling systems at remote locations) may be communicatively coupled to the network so as to access data from the controller 220. The controller 220 also may be communicatively coupled to a remote real time operating center 228 at a remote location from the well site through the input/output devices 224 and/or the network 226, allowing the remote real time operating center 228 to control and receive data from the controller 220.

The controller 220 receives data from and controls other elements of the system 200 including: displaying and/or controlling the delivery pump 204 flow rate; displaying and/or controlling the heater 208 temperature; displaying and/or controlling the return pump 216 flow rate; displaying and/or controlling the blow back rate; displaying the density, flow rate, and temperature of the drilling mud measured by the meter 206; displaying the gas trap 210 temperature; displaying and/or controlling the gas trap 210 rotation rate; displaying and/or controlling the liquid trap 214 temperature.

In accordance with an exemplary embodiment of the present disclosure, once feeds from one or more sensors are obtained, they may be combined and used to identify various metrics. For instance, if there is data that deviates from normal expectancy at the rig site, the combined system may show another reading of the data from another sensor that may help identify the type of deviation. As would be appreciated by those of ordinary skill in the art, with the benefit of this disclosure, a control system may also collect data from multiple rig sites and wells to perform quality checks across a plurality of sites.

In certain embodiments, one or more fluid measurement devices that are configured to detect volumes, flow rates, and/or densities of one or more fluids introduced into or exiting the well bore may be positioned along one or more of the fluid lines feeding one or more fluids (e.g., drilling fluids) into the well bore and/or into one or more components of the systems of the present disclosure (e.g., a gas extractor and/or gas trap). These fluid measurement devices may include any type of sensor device known in the art capable of monitoring fluid volume or flow, including but not limited to acoustic sensors, nuclear sensors, Coriolis meters, Doppler radar, vortex flow meters or sensors, calorimetric flow meters or sensors, magnetic flow meters or sensors, electromagnetic meters or sensors, differential pressure meters or sensors, open channel meters or sensors, and the like. For example, the systems of the present disclosure may comprise a Coriolis meter or other fluid measurement device adjacent to the gas trap that is configured to measure the fluid density of fluids entering the gas trap for extraction. These fluid measurement devices may be communicatively coupled to a control system and/or information handling system that, among other things, uses data from those sensors to perform calculations in the methods of the present disclosure as described above.

An embodiment of the present disclosure is a well site gas extraction and analysis system that includes: a gas trap configured to extract one or more gaseous samples from a fluid at a well site before the fluid is circulated in a wellbore, the gaseous sample comprising one or more gas species; a gas analyzer configured to receive one or more gaseous samples from the gas extraction system and generate data regarding the amount of the gas species in the gaseous sample; and an information handling system communicatively coupled to the gas analyzer, wherein the information handling system is configured to receive data from the gas analyzer regarding the amount of the gas species in the gaseous sample, and use data received from the gas analyzer to determine an extraction efficiency coefficient for the gas species. Optionally, the gas analyzer is further configured to generate data regarding the amount of the gas species extracted from the fluid as a function of time until there is substantially no incremental increase in the amount of gas extracted, and measure a total extracted amount of the gas species, and the information handling system is further configured to receive data from the gas analyzer regarding the amount of the gas species extracted from the fluid as a function of time, determine a diffusion coefficient based at least in part on the amount of the gas species extracted as a function of time, determine a total amount of the gas species in the fluid based at least in part on the diffusion coefficient and the total extracted amount of the gas species, and determine an extraction efficiency coefficient for the gas species based at least in part on the total amount of the gas species in the fluid and the total extracted amount of the gas species. Optionally, the gas trap is further configured to extract one or more gaseous samples from a fluid at the well site after the fluid has been circulated in at least a portion of the wellbore and circulated to the surface, and the information handling system is further configured to use the extraction efficiency coefficient for the gas species to determine the amount of the gas species in the sample of the fluid circulated in at least a portion of the wellbore and circulated to the surface. Optionally, the information handling system is configured to determine the extraction efficiency coefficient for the gas species substantially in or near real time. Optionally, the information handling system is communicatively coupled to a network to permit a remote information handling system communicatively coupled to the network to access data from the information handling system. Optionally, the well site gas extraction and analysis system further includes a fluid measurement device positioned adjacent the gas trap and communicatively coupled to the information handling system, the fluid measurement device being configured to measure the fluid density of the fluid. Optionally, the gas trap is configured to operate at one or more of a constant temperature, a constant pressure, and a constant fluid flow rate.

Another embodiment of the present disclosure is a method for determining a gas extraction efficiency coefficient at a well site that includes: providing a reference sample of a fluid at a well site; extracting gas from the reference fluid sample at a well site while measuring an amount of one or more gas species extracted as a function of time until there is substantially no incremental increase in the amount of gas extracted, and then measuring a total extracted amount of the gas species; determining a diffusion coefficient based at least in part on the amount of the gas species extracted as a function of time; determining a total amount of the gas species in the reference fluid sample based at least in part on the diffusion coefficient and the total extracted amount of the gas species; and determining an extraction efficiency coefficient for the gas species based at least in part on the total amount of the gas species in the reference fluid sample and the total extracted amount of the gas species. Optionally, the method further includes: circulating at least a portion of the fluid in a portion of the well bore and to the surface at the well site; extracting a gaseous sample from a sample of the fluid circulated to the surface; detecting a quantity of the gas species in the gaseous sample; and using the extraction efficiency coefficient for the gas species to determine the amount of the gas species in the sample of the fluid circulated to the surface. Optionally, one or more of the steps of determining a diffusion coefficient, determining a total amount of the gas species in the reference fluid sample, and determining an extraction efficiency coefficient for the gas species are performed at the well site. Optionally, the extraction efficiency coefficient for the gas species is determined substantially in or near real time with a wellbore operation at the well site. Optionally, the method further includes accessing data regarding one or more of the diffusion coefficient, the amount of the gas species extracted as a function of time, the total extracted amount of the gas species, the total amount of the gas species in the reference fluid sample, and the extraction efficiency coefficient for the gas species from a remote location. Optionally, the fluid includes a drilling fluid. Optionally, the one or more gas species includes hydrocarbons.

Another embodiment of the present disclosure is a method of drilling a wellbore that includes: providing a reference sample of a drilling fluid at a well site; extracting gas from the reference drilling fluid sample at a well site while measuring an amount of one or more gas species extracted as a function of time until there is substantially no incremental increase in the amount of gas extracted, and then measuring a total extracted amount of the gas species; determining a diffusion coefficient based at least in part on the amount of the gas species extracted as a function of time; determining a total amount of the gas species in the reference drilling fluid sample based at least in part on the diffusion coefficient and the total extracted amount of the gas species; determining an extraction efficiency coefficient for the gas species based at least in part on the total amount of the gas species in the reference fluid sample and the total extracted amount of the gas species; using the drilling fluid to drill at least a portion of a wellbore at the well site; circulating at least a portion of the drilling fluid to the surface at the well site; extracting a gaseous sample from a sample of the drilling fluid circulated to the surface; detecting a quantity of the gas species in the gaseous sample; and using the extraction efficiency coefficient for the gas species to determine the amount of the gas species in the sample of the drilling fluid circulated to the surface. Optionally, the extraction efficiency coefficient for the gas species is determined substantially in or near real time with using the drilling fluid to drill at least a portion of the wellbore at the well site. Optionally, the amount of the gas species in the sample of the drilling fluid circulated to the surface determined substantially in or near real time with using the drilling fluid to drill at least a portion of the wellbore at the well site. Optionally, the method further includes accessing data regarding one or more of the diffusion coefficient, the amount of the gas species extracted as a function of time, the total extracted amount of the gas species, the total amount of the gas species in the reference fluid sample, and the extraction efficiency coefficient for the gas species from a remote location. Optionally, the one or more gas species includes hydrocarbons.

Therefore, the present disclosure is adapted to carry out the claimed methods and systems. While the disclosure has been depicted and described by reference to exemplary embodiments of the disclosure, such a reference does not imply a limitation on the disclosure, and no such limitation is to be inferred. The disclosure is capable of considerable modification, alteration, and equivalents in form and function, as will occur to those ordinarily skilled in the pertinent arts and having the benefit of this disclosure. The depicted and described embodiments of the disclosure are exemplary only, and are not exhaustive of the scope of the disclosure. Consequently, the disclosure is intended to be limited only by the scope of the appended claims, giving full cognizance to equivalents in all respects. The terms in the claims have their plain, ordinary meaning unless otherwise explicitly and clearly defined by the patentee.

What is claimed is:

1. A well site gas extraction and analysis system comprising:
    a gas trap configured to extract one or more gaseous samples from a fluid at a well site before the fluid is circulated in a wellbore, the gaseous sample comprising one or more gas species;
    a gas analyzer configured to receive one or more gaseous samples from the gas extraction system and generate data regarding the amount of the gas species in the gaseous sample; and
    an information handling system communicatively coupled to the gas analyzer, wherein the information handling system is configured to
        receive data from the gas analyzer regarding the amount of the gas species in the gaseous sample, and
        use data received from the gas analyzer to determine an extraction efficiency coefficient for the gas specie, wherein the extraction efficiency coefficient is a ratio of the amount of gas extracted from the fluid to the amount of gas originally contained in the fluid.

2. The well site gas extraction and analysis system of claim 1 wherein:
    the gas analyzer is further configured to generate data regarding the amount of the gas species extracted from the fluid as a function of time until there is substantially no incremental increase in the amount of gas extracted, and measure a total extracted amount of the gas species;
and
    the information handling system is further configured to
        receive data from the gas analyzer regarding the amount of the gas species extracted from the fluid as a function of time,
        determine a diffusion coefficient based at least in part on the amount of the gas species extracted as a function of time,
        determine a total amount of the gas species in the fluid based at least in part on the diffusion coefficient and the total extracted amount of the gas species, and
        determine an extraction efficiency coefficient for the gas species based at least in part on the total amount of the gas species in the fluid and the total extracted amount of the gas species.

3. The well site gas extraction and analysis system of claim 2 wherein: the gas trap is further configured to extract one or more gaseous samples from a fluid at the well site after the fluid has been circulated in at least a portion of the wellbore and circulated to the surface; and
    the information handling system is further configured to use the extraction efficiency coefficient for the gas species to determine the amount of the gas species in the sample of the fluid circulated in at least a portion of the wellbore and circulated to the surface.

4. The well site gas extraction and analysis system of claim 1 wherein:
    the gas trap is further configured to extract one or more gaseous samples from a fluid at the well site after the fluid has been circulated in at least a portion of the wellbore and circulated to the surface; and
    the information handling system is further configured to use the extraction efficiency coefficient for the gas species to determine the amount of the gas species in the sample of the fluid circulated in at least a portion of the wellbore and circulated to the surface.

5. The well site gas extraction and analysis system of claim 1 wherein the information handling system is configured to determine the extraction efficiency coefficient for the gas species substantially in or near real time.

6. The well site gas extraction and analysis system of claim 1 wherein the information handling system is communicatively coupled to a network to permit a remote information handling system communicatively coupled to the network to access data from the information handling system.

7. The well site gas extraction and analysis system of claim 1 further comprising a fluid measurement device positioned adjacent the gas trap and communicatively coupled to the information handling system, the fluid measurement device being configured to measure the fluid density of the fluid.

8. The well site gas extraction and analysis system of claim 1 wherein the gas trap is configured to operate at one or more of a constant temperature, a constant pressure, and a constant fluid flow rate.

9. A method for determining a gas extraction efficiency coefficient at a well site, the method comprising:
    providing a reference sample of a fluid at a well site;
    extracting gas from the reference fluid sample at a well site using a gas trap while measuring an amount of one or more gas species extracted as a function of time using a gas analyzer until there is substantially no incremental increase in the amount of gas extracted, and then measuring a total extracted amount of the gas species;
    determining a diffusion coefficient based at least in part on the amount of the gas species extracted as a function of time;

determining a total amount of the gas species in the reference fluid sample based at least in part on the diffusion coefficient and the total extracted amount of the gas species; and determining an extraction efficiency coefficient for the gas species based at least in part on the total amount of the gas species in the reference fluid sample and the total extracted amount of the gas species, wherein the extraction efficiency coefficient is a ratio of the amount of gas extracted from the fluid to the amount of gas originally contained in the fluid.

10. The method of claim 9 further comprising:

circulating at least a portion of the fluid in a portion of the well bore and to the surface at the well site;

extracting a gaseous sample from a sample of the fluid circulated to the surface; detecting a quantity of the gas species in the gaseous sample; and using the extraction efficiency coefficient for the gas species to determine the amount of the gas species in the sample of the fluid circulated to the surface.

11. The method of claim 9 wherein one or more of the steps of determining a diffusion coefficient, determining a total amount of the gas species in the reference fluid sample, and determining an extraction efficiency coefficient for the gas species are performed at the well site.

12. The method of claim 9 wherein the extraction efficiency coefficient for the gas species is determined substantially in or near real time with a wellbore operation at the well site.

13. The method of claim 9 further comprising accessing data regarding one or more of the diffusion coefficient, the amount of the gas species extracted as a function of time, the total extracted amount of the gas species, the total amount of the gas species in the reference fluid sample, and the extraction efficiency coefficient for the gas species from a remote location.

14. The method of claim 9 wherein the fluid comprises a drilling fluid.

15. The method of claim 9 wherein the one or more gas species comprises hydrocarbons.

16. A method of drilling a wellbore, the method comprising:

providing a reference sample of a drilling fluid at a well site;

extracting gas from the reference drilling fluid sample at a well site using a gas trap while measuring an amount of one or more gas species extracted as a function of time using a gas analyzer until there is substantially no incremental increase in the amount of gas extracted, and then measuring a total extracted amount of the gas species;

determining a diffusion coefficient based at least in part on the amount of the gas species extracted as a function of time;

determining a total amount of the gas species in the reference drilling fluid sample based at least in part on the diffusion coefficient and the total extracted amount of the gas species;

determining an extraction efficiency coefficient for the gas species based at least in part on the total amount of the gas species in the reference fluid sample and the total extracted amount of the gas species, wherein the extraction efficiency coefficient is a ratio of the amount of gas extracted from the fluid to the amount of gas originally contained in the fluid;

using the drilling fluid to drill at least a portion of a wellbore at the well site; circulating at least a portion of the drilling fluid to the surface at the well site;

extracting a gaseous sample from a sample of the drilling fluid circulated to the surface;

detecting a quantity of the gas species in the gaseous sample; and using the extraction efficiency coefficient for the gas species to determine the amount of the gas species in the sample of the drilling fluid circulated to the surface.

17. The method of claim 16 wherein the extraction efficiency coefficient for the gas species is determined substantially in or near real time with using the drilling fluid to drill at least a portion of the wellbore at the well site.

18. The method of claim 16 wherein the amount of the gas species in the sample of the drilling fluid circulated to the surface determined substantially in or near real time with using the drilling fluid to drill at least a portion of the wellbore at the well site.

19. The method of claim 16 further comprising accessing data regarding one or more of the diffusion coefficient, the amount of the gas species extracted as a function of time, the total extracted amount of the gas species, the total amount of the gas species in the reference fluid sample, and the extraction efficiency coefficient for the gas species from a remote location.

20. The method of claim 16 wherein the one or more gas species comprises hydrocarbons.

* * * * *